United States Patent [19]

Meng

[11] Patent Number: 5,554,540
[45] Date of Patent: Sep. 10, 1996

[54] METHOD AND APPARATUS FOR PRESERVING THE SENSITIVITY OF A THERMIONIC IONIZATION DETECTOR

[75] Inventor: Chinkai Meng, Hockessin, Del.

[73] Assignee: Hewlett-Packard Company, Palo Alto, Calif.

[21] Appl. No.: 375,019

[22] Filed: Jan. 19, 1995

[51] Int. Cl.$^6$ .................................................. G01N 30/02
[52] U.S. Cl. ........................... 436/153; 422/68.1; 422/70; 422/89
[58] Field of Search ............................ 422/68.1, 70, 83, 422/89, 90, 98; 436/103, 106, 153

[56] References Cited

U.S. PATENT DOCUMENTS

| | | | |
|---|---|---|---|
| 3,859,209 | 1/1975 | Jahnsen et al. . | |
| 4,202,666 | 5/1995 | Hall et al. . | |
| 4,203,726 | 5/1980 | Patterson | 23/232 |
| 4,622,305 | 11/1986 | Patterson | 436/103 |
| 4,801,430 | 1/1989 | Robbat et al. | 422/52 |
| 4,873,862 | 10/1989 | Scott | 73/23.1 |
| 4,883,958 | 11/1989 | Vestal | 250/288 |
| 4,958,529 | 9/1990 | Vestal | 73/864.81 |
| 4,994,096 | 2/1991 | Klein et al. . | |
| 5,108,466 | 4/1992 | Klein et al. . | |
| 5,108,468 | 4/1992 | Ligon | 55/67 |

Primary Examiner—Lyle A. Alexander
Attorney, Agent, or Firm—Mark Z. Dudley

[57] ABSTRACT

Method and apparatus for the analysis of one or more analytes present in a sample that may be dissolved in a hostile solvent and carried in a first fluid. The first fluid is combined with a first detector fluid to provide a fluid mixture which flows across the surface of an ionization source. The analytes are ionized by means of an ionization process in which electrical charge is transferred from the ionization source and converted into gas phase ion species. The ion current is collected and measured at a collector electrode adjacent to the ionization source. The flow of the first detector fluid is reduced during the presence of the solvent at the ionization source so as to suppress a chemical reaction that heretofore would degrade the sensitivity of the detector.

8 Claims, 7 Drawing Sheets

METHOD AND APPARATUS FOR PRESERVING THE SENSITIVITY OF A THERMIONIC IONIZATION DETECTOR

FIELD OF THE INVENTION

The present invention relates generally to gas chromatography, and in particular to the operation of a thermionic ionization detector.

BACKGROUND OF THE INVENTION

Thermionic ionization detectors are used in the field of chromatography for the detection of specific constituent components (i.e., analytes) of a sample that are present in a carrier fluid stream. Such detectors usually include an ionization source having a surface impregnated with an alkali metal compound so as to make the detector specifically sensitive to a halogen, nitrogen, or phosphorus compound. An energy source, such as an electrical heating current carried by a resistive heating wire embedded in the ionization source, heats the ionization source. Certain sample compounds, or their decomposition products, extract the electrical charge from the hot thermionic surface of the source. Ions form at the ionization source and migrate through a fluid stream flowing past the ionization source to a collector electrode. The resulting ion current is collected at the collector electrode. An electronic current-measuring circuit, such as an electrometer, measures the ion current arriving at the collector electrode.

It is known that the sensitivity of a thermionic detector to the presence of analytes in the carrier fluid stream can be degraded by the presence of certain solvents in the carrier fluid stream- For example, the solution of a chlorinated solvent can cause a variation in the baseline output of the detector. The response of the detector to most analytes that are eluted thereafter is inaccurate; the detector is then considered to be unsuitable for most applications. Further, the chemical reaction that occurs between such and the ionization source has been found to damage the ionization source, thus shortening its useful life. Such solvents are accordingly considered herein as "hostile solvents".

Most, if not all, hostile solvents typically exhibit a short retention time and thus their solution can be predicted. One prior art thermionic detection technique therefore attempts to divert the carrier fluid stream from the detector during the elution of the offensive solvents. See, for example, U.S. Pat. No. 3,859,209. Another prior art approach is to decrease the heating current present in the bead when the solvent is eluted. The bead temperature is thereby said to be correspondingly decreased to a temperature that does not support the destructive reaction on the source. See, for example, U.S. Pat. No. 4,202,666.

However, the aforementioned approaches have significant drawbacks. The addition of a valve to divert the carrier fluid stream introduces a dead volume and an additional reactive surface into the fluid stream. This approach is also more costly and complex to implement than is desirable. The practice of lowering the bead temperature has been found to cause the baseline response of the detector to be severely reduced for a delay that is significantly longer than acceptable. That is, the detector output level decreases to an unusable level and the detector output level does not return its original value for as long as a minute or more. Such a delay is beyond the elution time of many of the analytes of interest. As a result, the solution of some analytes cannot be detected with accuracy, and the detector is considered unreliable. Further, the thermal shock that is caused by temperature cycling can shorten the bead lifetime.

SUMMARY OF THE INVENTION

This invention provides a method and apparatus for an improvement in the thermionic ionization detection of one or more analytes in a sample that may be dissolved in a hostile solvent.

In a first preferred embodiment of the present invention, an analytical instrument may be constructed to include a pneumatic controller for providing a selectable flow of each of a plurality of fluids, said plurality including a detector support fluid; fluid mixture means for providing a fluid mixture of detector support fluid, carrier fluid, an analyte, and a solvent; thermionic ionization detector, operably connected to the fluid mixture means for receiving the fluid mixture, and operably connected to the fluid controller for receiving a selectable flow of the detector support fluid, wherein the elution of the solvent at the thermionic ionization detector occurs in a solvent elution period; and a programmable computer for effecting a reduction in the initial flow of the detector support fluid to a reduced flow for a predetermined flow reduction period, and wherein the flow reduction period is coordinated with the solvent elution period.

In a second preferred embodiment of the present invention, a chromatograph may be constructed to include a separation column for providing a column fluid comprising a fluid mixture of a carrier fluid, an analyte, and a solvent, a thermionic ionization detector, including a fluid mixing structure for receiving a plurality of fluids, the plurality including the column fluid and a detector support fluid, an ionization source having a matrix including an alkali metal compound that is capable of ionization of the analyte to produce an ion current, a collector electrode for receiving the ion current, and a fluid-directing structure for aligning the ionization source and the collector electrode in a spaced relationship and for directing the column fluid and detector support fluid in contact with the ionization source to the collector electrode. A programmable computer is provided for determining the presence of the solvent at the ionization source and for providing a control signal according to the determination, the control signal being directed to effect a reduction in the detector support fluid for a predetermined period that is coordinated with the presence of the solvent at the ionization source. A pneumatic controller is provided for controlling the flow of the detector support fluid to the thermionic ionization detector in accordance with the control signal.

DETAILED DESCRIPTION OF THE PREFERRED EMBODIMENTS

The present invention will find useful application in a variety of fluid analysis systems that benefit from thermionic ionization detection of one or more particular constituent components of a sample present in a fluid. Such systems are commonly employed in a wide variety of applications, such as sample analysis or purification, chemical analysis, clinical assay, environmental monitoring or sensing, industrial processing, and water purification.

The apparatus and methods of the present invention may be employed to improve the detection of an analyte that may be present in a variety of fluids. Such fluids are intended to include gases, liquids, multiple component gases and liquids, and mixtures thereof capable of regulated flow. Gases are the preferred fluids according to the practice of the present invention, and therefore the following description of the invention will be directed to a gas chromatographic analytical system (hereinafter, a chromatograph). Further examples that are particularly benefited by use of the present invention include supercritical fluid chromatography and high pressure gas chromatography. However, it should be understood that the teachings herein are applicable to analysis of other fluids.

Figure 1:
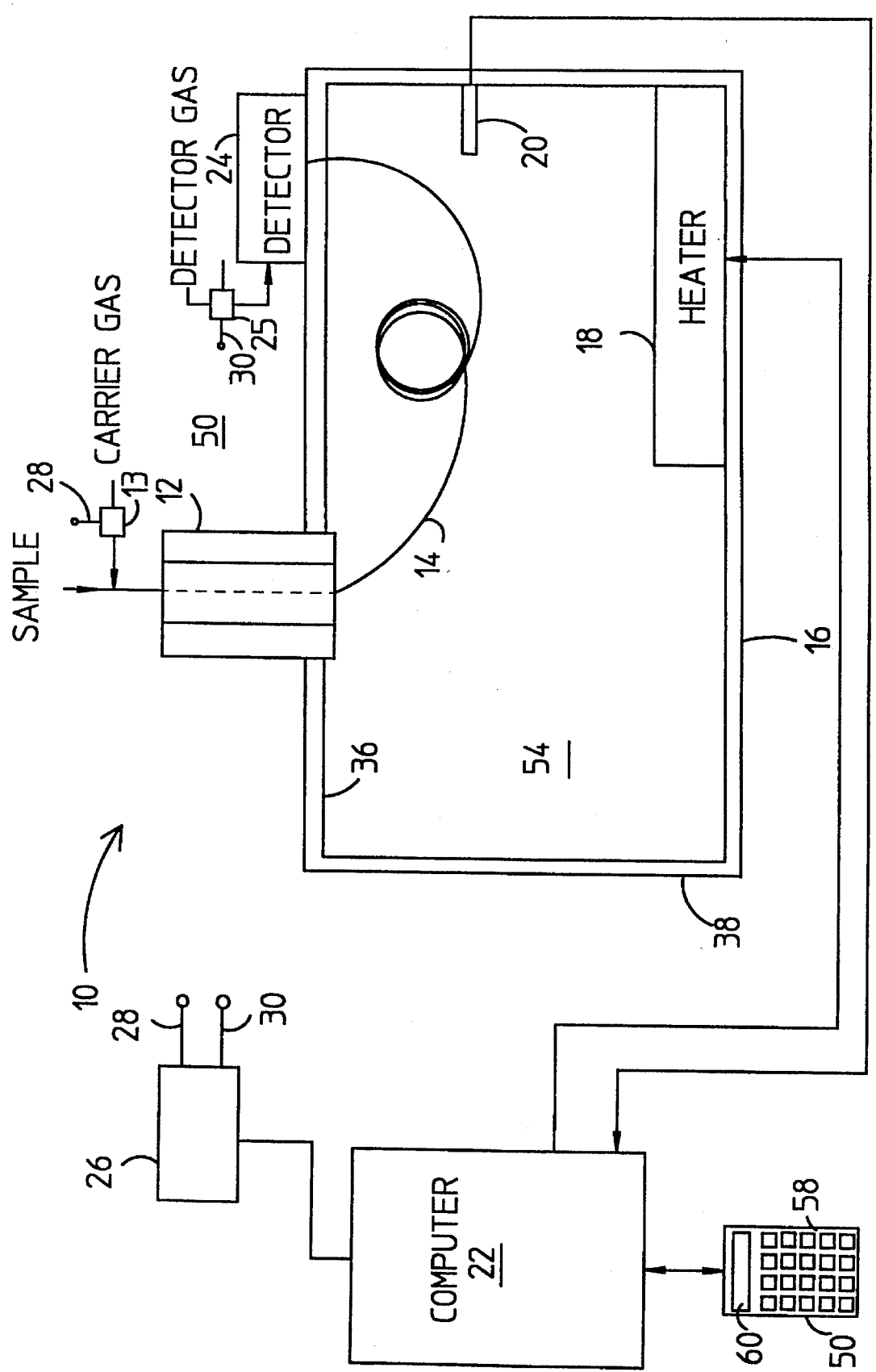
FIG. 1 is simplified schematic representation of a chromatograph constructed according to the present invention.

A new and novel analytical instrument is shown in FIG. 1 and is generally designated as chromatograph 10. In the preferred embodiment, the chromatograph 10 is a Hewlett-Packard HP6890 gas chromatograph. In order to perform a chromatographic separation of a given sample compound, the sample is injected with a pressurized carder gas by means of an injection port 12. The carrier gas supplied to injection port 12 is, provided from a source through an appropriate carder gas valve 13, which serves to control the pressure of the carrier gas. The injection port 12 may be constructed to heat, and thereby vaporize, the sample during injection. The carrier gas valve 13 is operated under the control of the computer 22 by way of a control signal provided on a control line 28 from a pneumatic controller 26. A column 14 is positioned within an oven 16. Although no particular oven design is necessary in order to comply with the principles of the present invention, the oven preferably includes a heating unit 18 and a temperature sensor 20. In order to ensure that the temperature within the oven is at a desired level, sensor 20 generates a feedback signal representative of the temperature in oven 16, which signal is provided to computer 22. Heating unit 18 provides heat to oven 16 in response to a control signal generated by computer 22. A column fluid including the carrier gas/sample combination passing through column 14 is exposed to a temperature profile resulting in part from the operation of heater 18 within oven 16. During this profile of changing temperatures, the sample will separate into its components primarily due to differences in the interaction between the sample components and the column coating at a given temperature.

As the components exit column 14 they are detected by a thermionic ionization detector (hereinafter, detector) 24. A plurality of detector support fluids of appropriate types, such as air, hydrogen, and make-up gas, are provided from a source (not shown) to the detector 24. As illustrated, one such detector support fluid in particular is provided through a valve 25 under the control of the pneumatic controller 26 by way of control line 30. Valve 25 is open and closed in relation to a control signal received by the pneumatic controller 26 from computer 22. The pneumatic controller 26 effects control of, among other things, the time during which valve 13 and valve 25 remain open and closed in relation to certain operating conditions of the system 10. In particular, and in accordance with a feature of the present invention, the valve 25 is controlled to decrease the flow of a detector support fluid composed of hydrogen gas to the detector 24 during the elution of a hostile solvent.

Computer 22 maintains overall control of all systems associated with gas chromatograph 10. It will be recognized that any particular gas chromatograph may include more systems than those described in relation to the present invention. It will also be understood that although computer 22 is shown as a single block, such computer includes a central processing unit and all associated peripheral devices, such as random access memories, read-only memories, input/output isolation devices, clocks and other related electronic components. In the preferred embodiment, the central processor used in computer 22 is a microprocessor. As such, computer 22 includes a memory in which information and programming can be stored and retrieved by known methods. However, it will be appreciated that the programmed control of pneumatic controller 26 can be implemented by other computing means, such as an embedded microprocessor or dedicated controller circuit incorporated in the pneumatic controller 26. Also, the programming associated with computer 22 that is utilized in relation to the present invention will be readily understood from the description herein.

An electronic control panel 50 is shown to include at least two main input/output components, namely a keypad 58, and a display 60. By monitoring the operation of the chromatograph 10 by signals from sensors such as sensor 20, 22 computer can initiate and maintain certain functions required for an analytical run. Consequently, indicating or prompt messages can be generated by computer 22 and displayed on display 60. Operating commands and other information are entered into computer 22 by way of keypad 58. The particular messages displayed on display 60 and the information entered through keypad 58 which relates to the present invention are described below in reference to FIGS. 4A, 413, 4C, and 4D.

Figure 2:
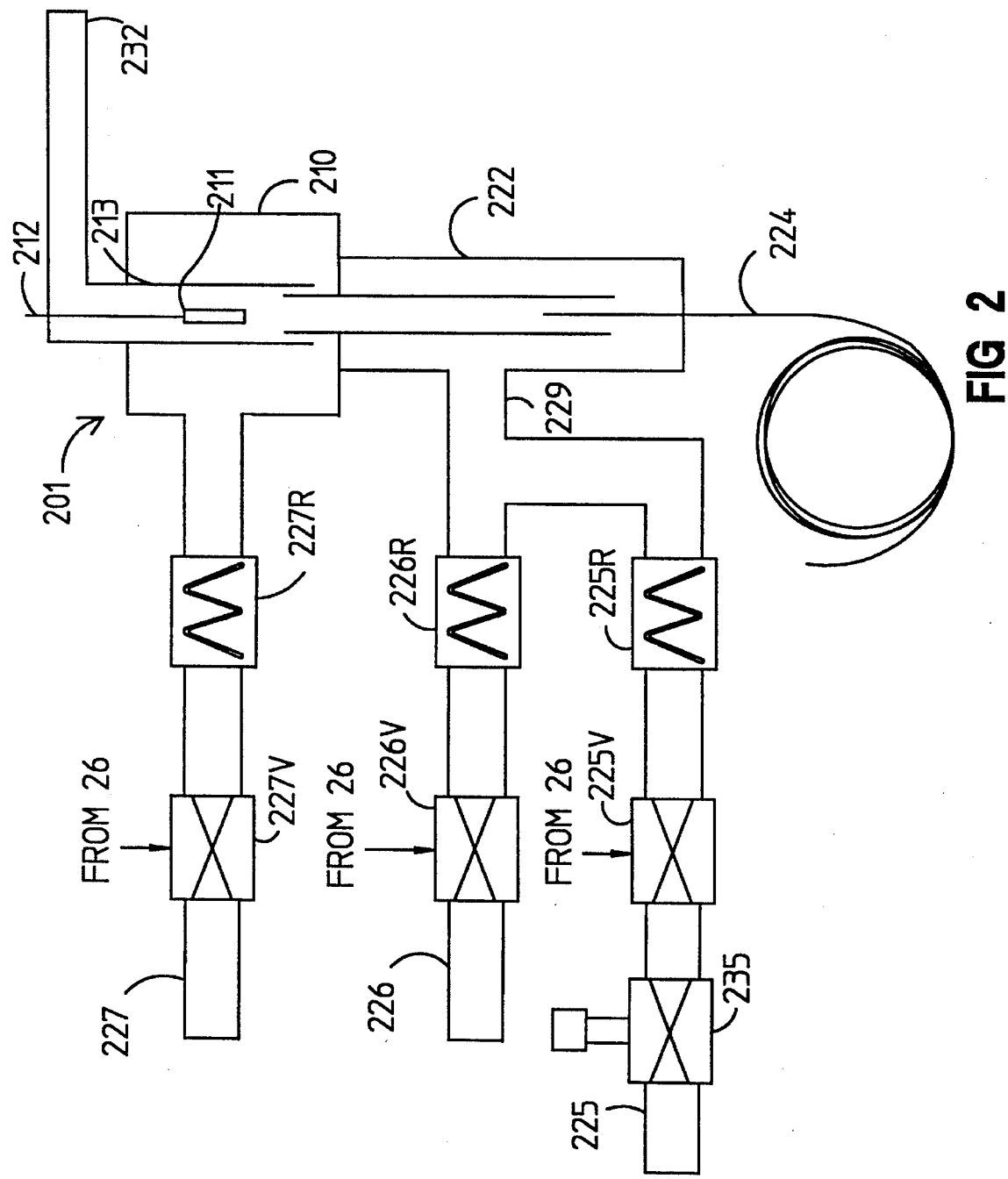
FIG. 2 is a simplified cross-sectional illustration of a portion of the chromatograph of FIG. 1, showing a first configuration of a pneumatic control section and a thermionic ionization detector constructed according to the present invention.

FIG. 2 shows a schematic illustration of a pneumatic control section and a first preferred embodiment of a thermionic ionization detector 201 constructed to include an ionization source 211, a bead heater line 212, and a collector electrode 213. The ionization source 211 and the collector electrode 213 are coaxially aligned and closely fitted to the interior of a passageway defined by a fluid-directing structure 210. An electronic power supply (not shown) provides a controlled amount of electrical, current or voltage on bead heater line 212 to cause a selectable amount of heat energy in the ionization source 211. The heat energy, absorbed by the ionization source 211, causes the ionization source to achieve a predetermined elevated temperature. In response, alkali metal atoms in the surface of the ionization source 211 effect a surface of low work function which is capable of transferring electrical charge while operated at the elevated temperature. The collector electrode 213 is electrically connected to an ion current measurement device (not shown) such as an electrometer which is used to measure the magnitude of ionization current that flows from the ionization source to the collector electrode 213.

A fluid mixing structure 222 communicates with the fluid-directing structure 210 for directing the following fluids toward the ionization source 211: a column fluid supplied on a column fluid supply line 224, a make-up fluid supplied on a make-up fluid line 225, a first detector support fluid supplied on a first detector support fluid line 226, and a second detector fluid supplied on a second detector support fluid line 227. Preferably, the column fluid supply line 224 is integral with the column 14 and hence the column fluid comprises a heated, gaseous combination (under pressure) of the sample that is to be analyzed and a carrier gas. The make-up fluid also preferably comprises carrier gas; the first detector support fluid preferably comprises pressurized hydrogen gas; and the second detector fluid comprises air at ambient pressure and temperature. The make-up fluid and the first detector support fluid are combined via a conduit 229 connected between the fluid mixing structure 222, the make-up fluid line 225, and the first detector support fluid line 224. Also included are a make-up fluid pressure regulator 235, a make-up fluid valve 225V, and a make-up fluid restrictor 225R; first detector fluid valve 226V and restrictor 226R; and second detector fluid valve 227V and restrictor 227R. The valves 225V, 226V, and 227V are preferably solenoid valves that are subject to the control of the pneumatic controller 26 as will be described in greater detail below.

The aforementioned fluids combine to form a fluid mixture that is restricted to pass the ionization source 211 and the collector electrode 213. Accordingly, the contact of the fluid mixture with the ionization source 211 causes a chemical reaction and a related ionization mechanism to occur at the ionization source 211. However, in a departure from the prior art, the content of the fluid mixture is temporarily altered during the time of elution of a hostile solvent, so as to suppress at least some aspect of the chemical reaction, so as to preserve the sensitivity of the detector 201. The ionization source ionizes organic molecules in the fluid mixture that contain nitrogen (N) and phosphorous (P). The ions are collected at the collector electrode 213, and the resulting ion current is measured to provide a chromatogram, A vent tube 232 allows the further passage of the fluid mixture from the detector 201 to an analytical instrument (not shown), such as a mass spectrometer, that may be optionally included for further analysis of the fluid mixture as known in the art. In the preferred application of the above-described detector 201, the column fluid flow is taken from the effluent gas stream of a separation column in a gas chromatograph instrument. However, the preferred embodiment of the present invention is not limited in application to use as a thermionic ionization detector for a gas chromatograph instrument. Because the contemplated ionization source 111 provides selective ionization of certain types of chemical substances, this source can also be used in the detection of the presence of these specific chemical substances in any fluid environment. It is also recognized that the preferred embodiment of the present invention can be modified for use as a means of converting molecules of certain types of chemical substances into gas phase negative ions for the purpose of subsequent analysis of charge-to-mass ratio by a mass spectrometer instrument, or mass and size analysis by an ion mobility apparatus. For such applications, the vent tube 232 would be plumbed to allow the passage of gas phase ions into the subsequent analysis equipment.

The ionization source 211 is preferably formed of one or more alkali-metal compounds set in a matrix or substrate. In the preferred embodiment, the ionization source 211 is composed of matrix of fused silica or fused quartz that has been enriched with one or more alkali-metal compounds. An alternative composition would include a hardened ceramic material that includes one or more alkali-metal compounds. Generally, the amount and type of alkali-metal compound are selected according to the intended type of surface ionization process sought. Alkali metal compound additives may include compounds of any of the class of alkali metals that includes Cs, Rb, K, Ns, and Li, and in some instances may include a combination of more than one type of alkali metal compound. Alkali sulfate compounds, alkali carbonates, and alkali chlorides may be suitable.

Figure 3:
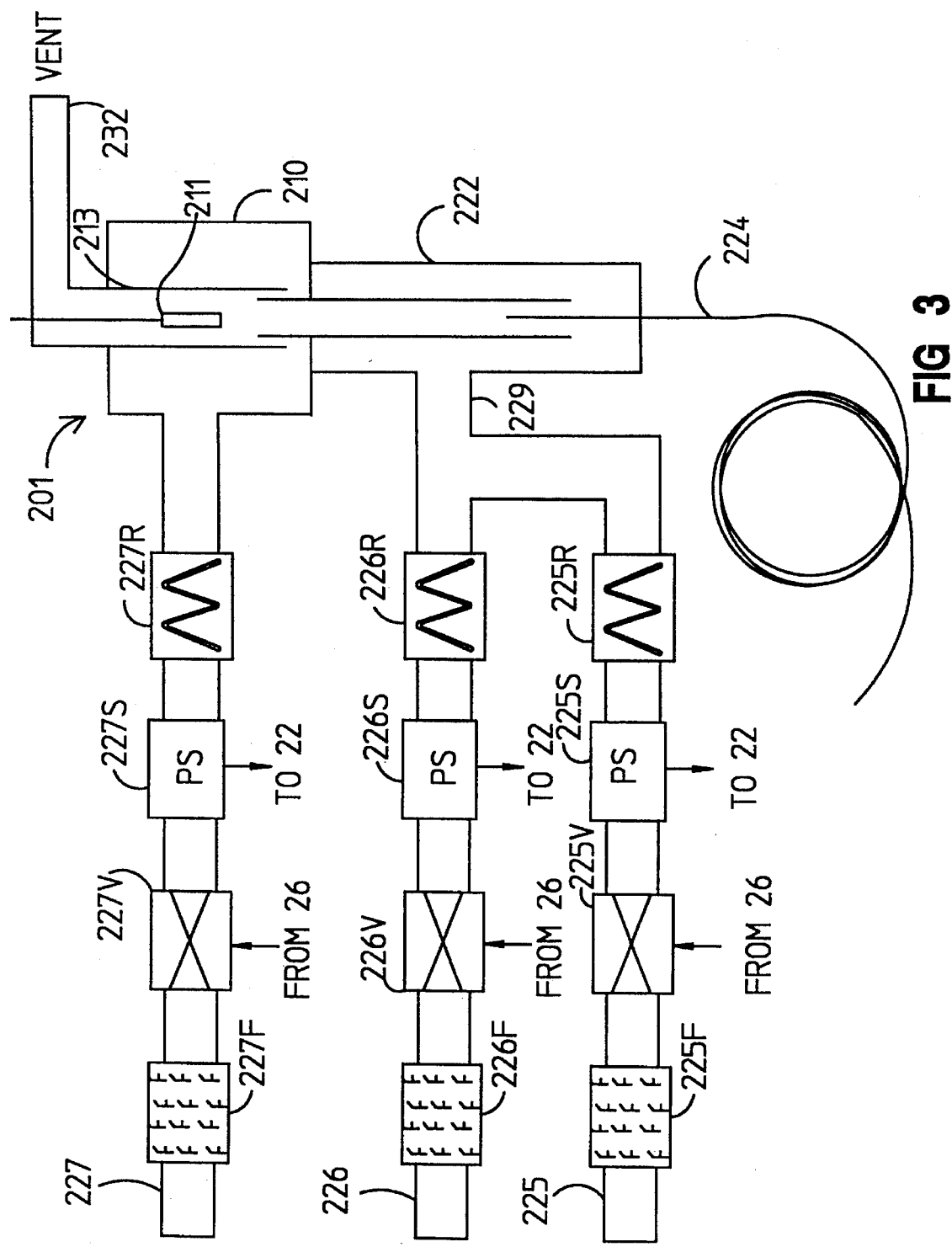
FIG. 3 is a simplified cross-sectional illustration of the portion of the chromatograph of FIG. 1, showing a second configuration of the pneumatic control section.

FIG. 3 illustrates an alternative embodiment of the pneumatic control section of FIG. 2. In FIG. 3, the valves 225V, 226V, and 227V are preferably provided in the form of proportional valves that are subject to the control of the pneumatic controller 26 according to signals received by the computer 22 from sensors 225S, 226S, and 227S, as will be described in greater detail below. Preferably, such sensors are pressure sensors that provide sense signals indicative of the respective pressures in the make-up fluid line 225, first detector support fluid line 226, and second detector support fluid line 227. Also provided are respective filter frits 225F, 226F, and 227F.

In the embodiments illustrated in FIGS. 2 and 8, the computer 22 controls the flow of the make-up fluid, the column fluid, the first detector support fluid, and the second detector support fluid by transmitting an appropriate signal to the pneumatic controller 26, which in turn provides respective signals to a particular valve to increase or decrease the amount of fluid flowing therethrough to the detector 201. In the embodiment illustrated in FIG. 3, sensors 225S, 226S, 227S each sense a particular fluid parameter, such as fluid pressure or fluid flow, and transmits a feedback signal representative of such parameter to the computer 22. By monitoring the sense signals from sensors 225S, 226S, 227S, the computer 22 can effect near-instantaneous alteration of the flow of each fluid that is provided to the detector at any desired time. In particular, the fluid flow control in the embodiment illustrated in FIG. 8 is preferably provided via electronic pneumatic control (EPC). For further details of an electronic pneumatic control system, one may consult, for example, Klein, et al., U.S. Pat. No. 4,994,096 and U.S. Pat. No. 5,108,466, the disclosures of which are incorporated herein by reference.

In the preferred embodiment of the computer 22, the procedures necessary to set up or operate chromatograph 10, so that a particular gas chromatographic separation test or analytical run can be conducted, are automated. The contemplated automation allows the operator to program events using run time programming via a run table or by clock time programming. A plurality of timed events may be programmed in each run table for execution during an analytical run. Run time programming allows certain setpoints to change automatically during a run as a function of the chromatographic run time. For example, an event may be programmed to occur at 2 minutes after every injection. Such run time programming is contemplated as being applicable to the operation of the pneumatic controller, and particularly to the control of the first detector support fluid flow.

Figure 4A:
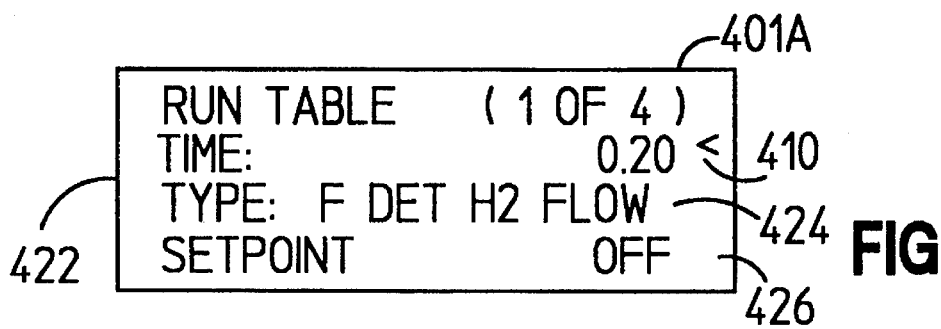
FIGS. 4A—4D are representations of successive run tables that are displayed on a control panel in the chromatograph of FIG. 1.
Figure 4B:
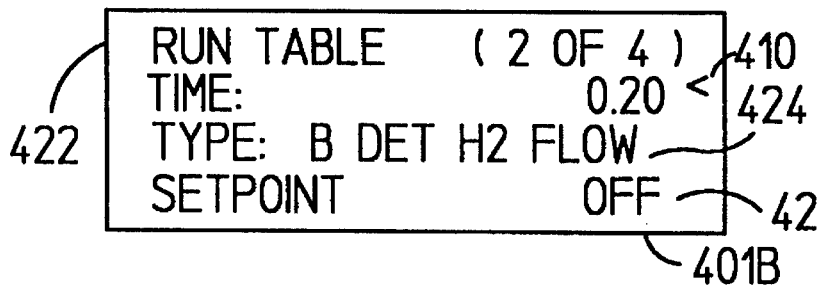
Figure 4C:
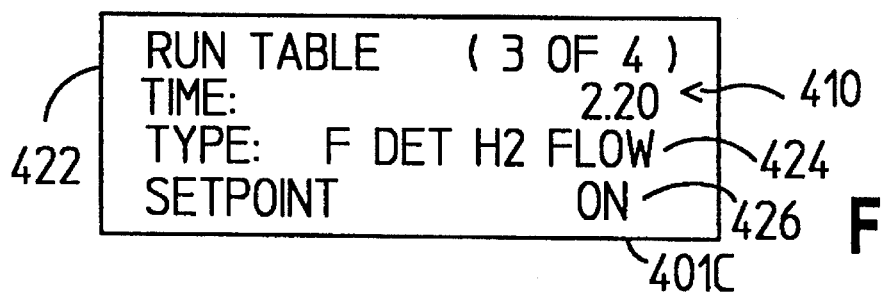

The run time programming of the operation of computer 22, and the operation of the pneumatic controller 26, which relate to and are in accordance with the present invention are illustrated in FIGS. 4A, 4B, 4C, and 4D. In the preferred embodiment, the operator may enter data regarding the operation of the pneumatic controller 26 into the computer 22 by use of the keypad 58. The computer 22 operates to store the entered information into memory in the form of one or more run tables for later access. The programmed events are arranged in order of execution time in a run table. Text denoting the characteristics of each event is displayed on the display 60. Preferably, the display 60 can sequentially display a series of windows 401A–401D each having four lines of text. A movable cursor 410 is provided to allow a line of text or a selected event type to be chosen by the operator, whereupon (as shown in FIG. 4C) the selected event is displayed in the window 401.

Two events that are pertinent to the present invention are a first event causing a reduction of flow of the first detector support fluid from an initial level to a reduced level, and a second event causing a resumption of the flow of the first detector support fluid to its initial level. The period of time that is programmed to occur between the first event and the second event may be considered as the flow reduction period. In the preferred embodiment, the reduction of flow is substantially to zero, and thus the first detector support fluid flow is set to "off". However, it is contemplated that in other embodiments the first detector support fluid flow may be set to a selectable proportion of the initial flow, such as a reduction by one-half. Also in the preferred embodiment, the first detector support fluid is provided as hydrogen gas.

Figure 4D:
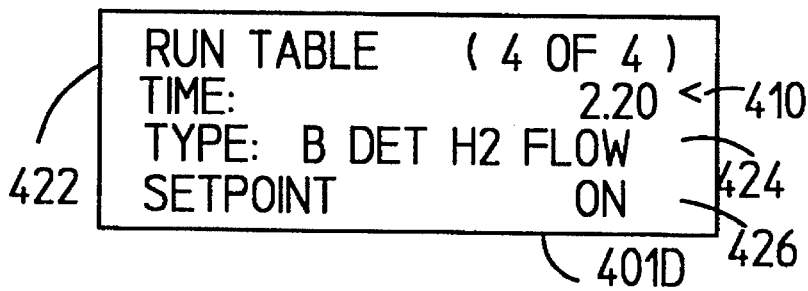

In the preferred embodiment of the chromatograph 10, detector 24 is provided as a plurality of separately located detectors, e.g., a front detector and a back detector. Accordingly, one event may be displayed in a window 401A and succeeding events may be sequentially scrolled upwardly in the display 60 for subsequent display of successive windows 401B, 401C, 401D by use of a scrolling key on the keypad 58. As shown in FIGS. 4A and 4C, a pair of run tables may be programmed for control of the first detector support fluid flow (illustrated as "F dot H2 flow") to the front detector. As shown in FIGS. 4B and 4D, a second pair of run tables may be programmed for control of the first detector support fluid flow (illustrated as "B det H2 flow") to a back detector. Such control of the detector support fluid flow is but one of many examples of the text that can be displayed in the window 401; the display 60 may be caused to include a menu (not shown) of other selectable event types, which may also be scrolled through the window 401.

Thus, a respective selection of e detector support fluid flow event type causes the display of a respective run table that includes a time line 422, a type line 424, and a setpoint line 426. The location of the cursor 410 and subsequent entry of numerical data on the keypad 58 allows the operator to program a first event wherein the flow of the first detector support fluid is reduced from an initial value, and by similar steps, a second event wherein the flow of the first detector support fluid is made to resume flow at the initial value. By such programming, a reduction in the flow of the first detector support fluid to the ionization source 211 can be timed to occur over a selectable period that is coordinated with another period that occurs during the elution of a hostile solvent. Accordingly, and in a particular feature of the present invention, the reduction of the flow of the first detector support fluid during an eluting solvent peak will suppress the deleterious aspect of the chemical reaction that would otherwise occur at the ionization source due to the influence of the hostile solvent.

By the term "coordinated" it is meant that, in the preferred embodiment, a flow reduction period, characterized by the time that the flow of the first detector support fluid is reduced, is set to substantially overlap in time with a solvent elution period characterised by the presence (i.e., elution) of the hostile solvent at the detector. However, this coordination is also contemplated as including a less-than-complete overlap, such as an overlap of the solvent elution period by one-half of the flow reduction period. Of course, as the contemplated overlap of the solvent elution period by the flow reduction period is decreased, the desired suppression of the chemical reaction may be incomplete, and one may expect the benefits of the invention to decline accordingly.

Adequate suppression of the chemical reaction has been found to occur at levels of hydrogen flow that are in the range of zero to one-half of the initial flow. Adequate suppression of the chemical reaction is also believed to occur at levels of first detector support fluid flow that are in the range of less than approximately one percent of the total detector fluid flow (wherein the total detector fluid flow may be considered to be the combination of the column fluid, the first detector fluid, the second detector fluid, and the make-up fluid flow). Accordingly, the flow rate of the first detector fluid is preferably reduced to a level that is less than either; a) approximately half the initial flow rate of the first detector support fluid, or b) one percent of the total detector support fluid flow.

The desired suppression of the chemical activity has been found to suppress the ionization mechanism at the ionization source, and as a result the baseline of the output signal of the detector 24 will decrease, typically to less than approximately 3 picoAmperes (pA). However, upon the resumption of flow of the first detector fluid to the ionization source, the suppression of the ionization mechanism ends, and the baseline of the output signal of the detector 24 recovers to its initial level after a very short recovery period. With recovery of the detector output signal baseline to its initial value, the sensitivity of the detector 24 is also restored. The recovery period has been found to be less than approximately 30 seconds. Accordingly, the elution of analytes after the recovery period may be detected as usual, and the output signal of the detector 24 is thus not subject to the extended decline in sensitivity that is experienced in certain prior art approaches, as already described hereinabove.

Experimental Results

The advantages of the above-described embodiments were demonstrated in a sample injection repeatability experiment performed on a Hewlett-Packard HP6890 gas chromatograph that was equipped with electronic pneumatic control (EPC), a front nitrogen-phosphorous detector, and a back nitrogen-phosphorous detector. Samples were dissolved in a hostile solvent (methylene chloride) and injected using a Hewlett-Packard HP7673B autoinjector, and a Hewlett-Packard Chemstation was used for instrument control and data acquisition. Other relevant experimental conditions are listed in Tables 1 and 2.

TABLE 1

Sample Introduction Conditions

| Component or Function | Condition |
|---|---|
| inlet type | cool on-column |
| inlet pressure | 15 psi |
| column flow rate | 3 ml/min |
| carrier gas | Helium |
| column size | 30 m × 0.320 mm × 25 μm HP-5 |
| oven program | 60(1)/10/100(0)/30/250(5) |
| syringe size | 5 μL |
| injection volume | 1 μL |

TABLE 2

Detector Conditions

| Condition | Amount |
|---|---|
| sample formulation | 0.65 PPM Azobenzene, 1000 PPM Octadecane, and 1 PPM Malathion in methylene chloride |
| detector temperature | 300 °C. |
| H2 flow rate (ml/min) | 3 |
| air flow rate (ml/min) | 60 |
| makeup gas type | Helium |
| makeup gas flow rate (ml/min) | 5 |
| initial offset (pA) | 30 |

Figure 5A:
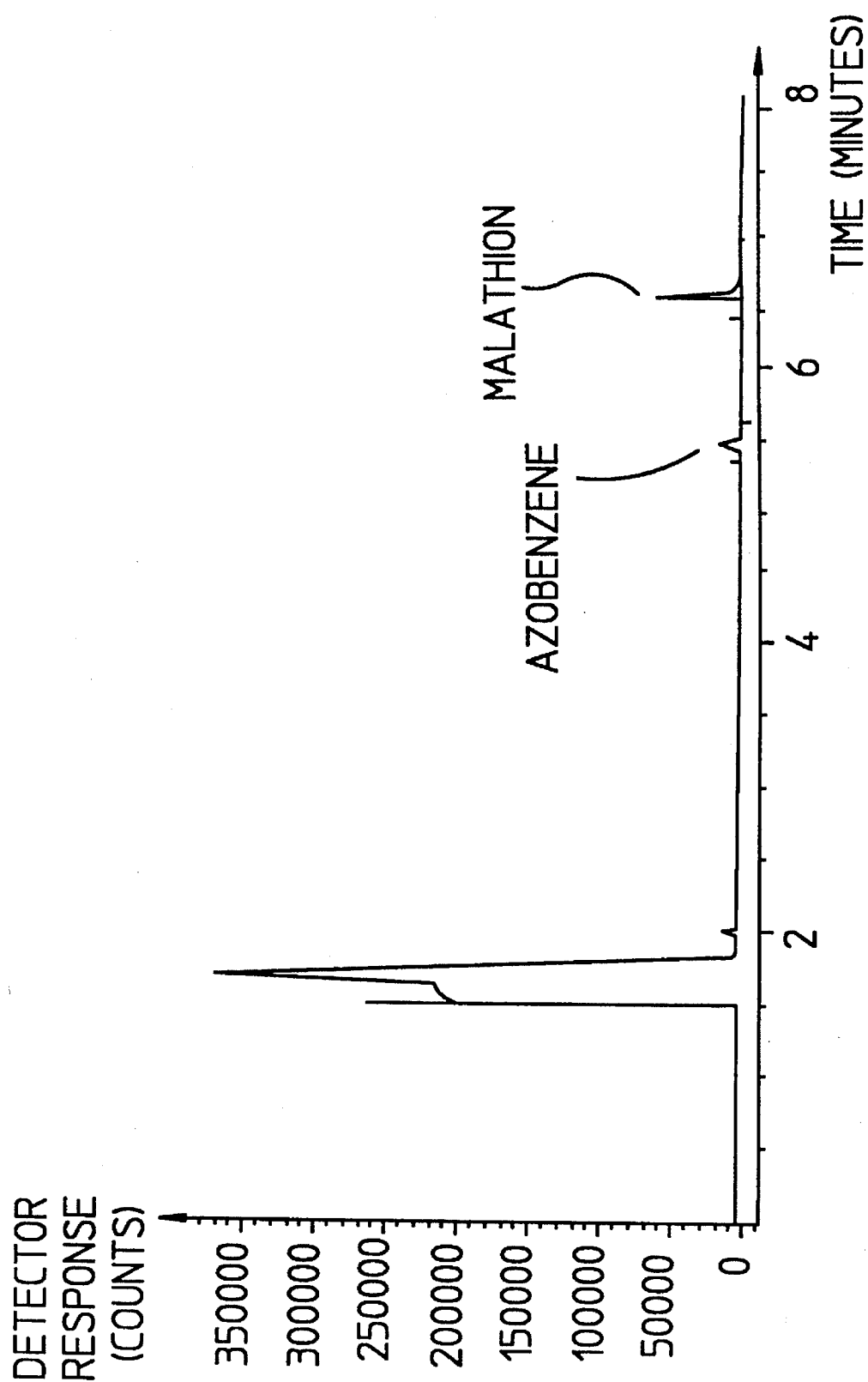
FIG. 5A is a chromatogram of a test sample processed by a chromatograph constructed according to the present invention, but without the operation and benefit of an inventive feature of the present invention.
Figure 5B:
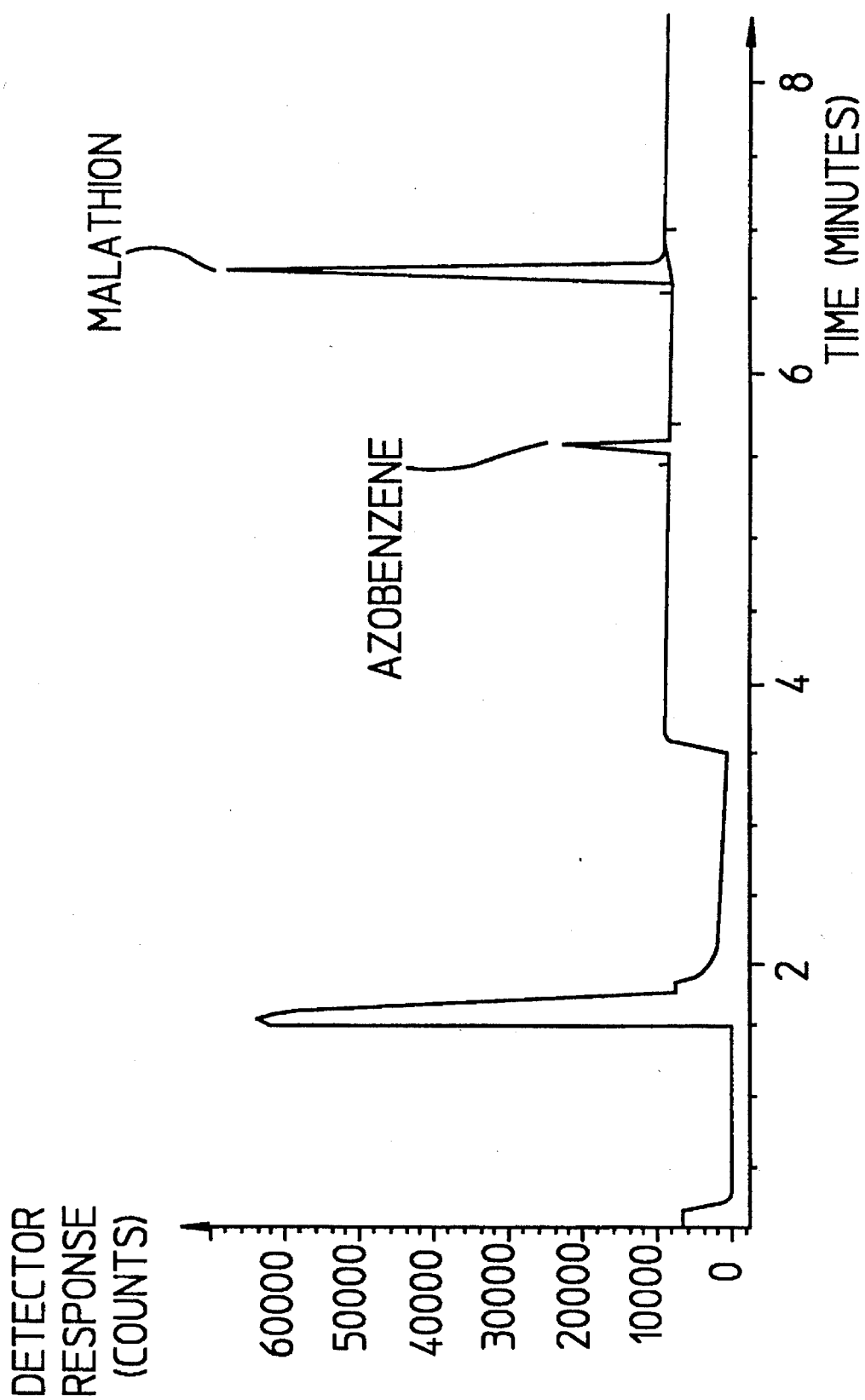
FIG. 5B is a chromatogram of the test sample processed as illustrated in FIG. 5A, but including the operation and benefit of an inventive feature of the present invention.

As shown in FIGS. 5A and 5B, the output level of the detector was recorded during the injection and separation of a series of test samples so as to provide respective chromatograms. Each test sample was composed of an identical mixture of Azobenzene and Malathion dissolved in methylene chloride. A first set of four test sample injections was performed with constant flow of hydrogen to the detector during the run. A second set of four test sample injections was performed with the hydrogen flow interrupted (i.e., switched to zero) at 0.2 minutes of run time and returned to its initial flow at 3.6 minutes of run time.

FIG. 5A depicts the chromatogram resulting from one of the first set of sample injections, which is characterized by uninterrupted (i.e., constant) hydrogen flow to the detectors. FIG. 5B depicts the chromatogram resulting from one of the second set of sample injections, which is characterized by interrupted (i.e., reduced) hydrogen flow to the detectors. As best illustrated in FIG. 5B, the detector output baseline drops as the hydrogen flow is stopped at approximately 0.2 minutes of runtime, but quickly recovers to the initial level within about 0.25 minutes of runtime.

Figure 6:
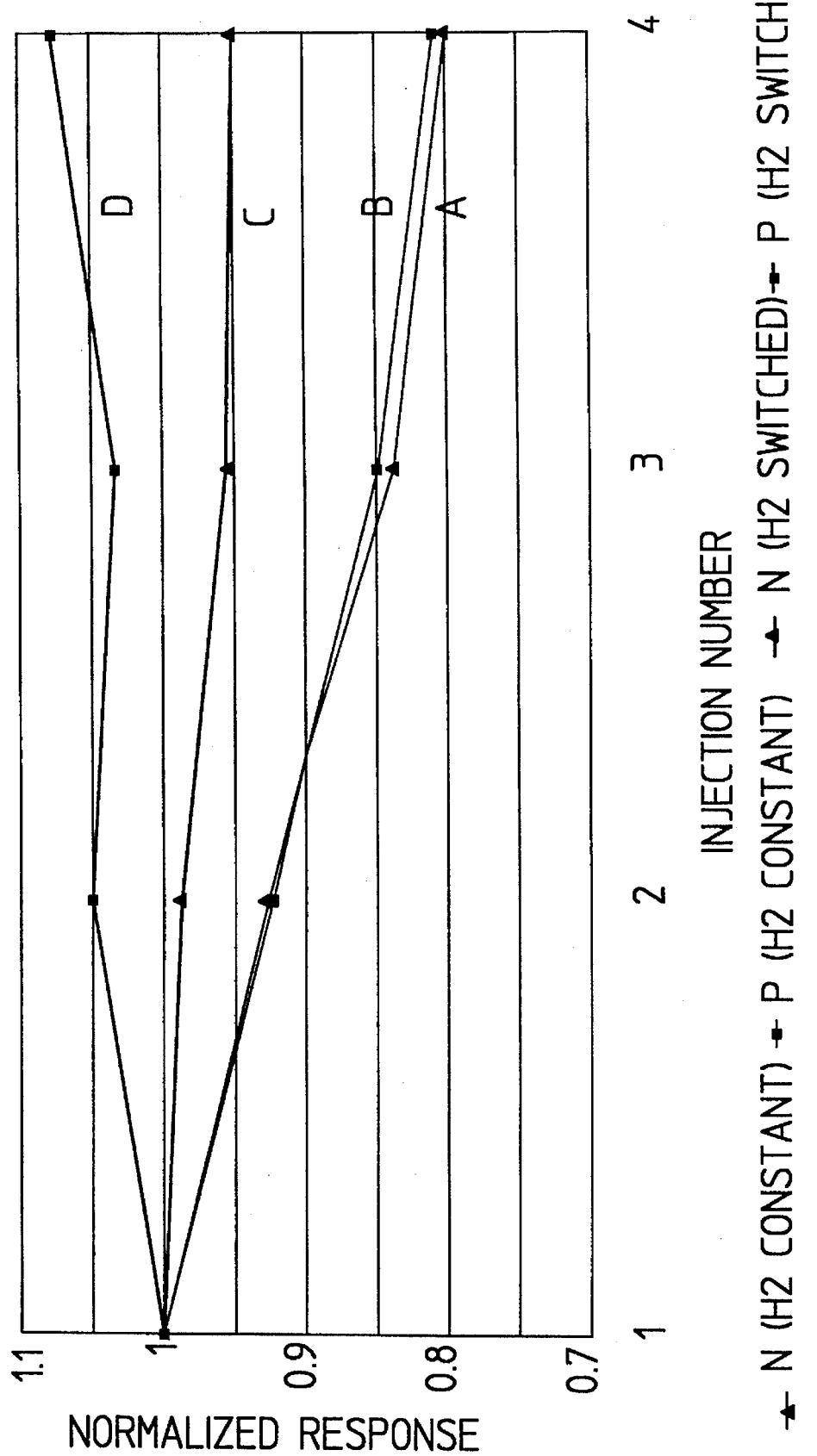
FIG. 6 is a graphical representation of the normalized peak areas realized in the detector output signal in a series of four injections, each series of injections being subject to a differing type of operation of the chromatograph of FIG. 1.

FIG. 6 shows first (A), second (B), third (C), and fourth (D) normalized responses of experienced in the prior art. In contrast, the third and fourth normalized peak responses (C), (D) may be seen to remain relatively stable as the number of injections increases, which indicates a preservation of the detector sensitivity, even while subjected to a hostile solvent.

Although the invention has been described with reference to the above-described preferred embodiments, variations and modifications are contemplated as being within the scope and spirit of the present invention.

What is claimed is:

1. An analytical instrument, comprising:
    a pneumatic controller, responsive to a control signal, for providing a selectable flow of a detector support fluid;
    fluid mixture means for providing a fluid mixture including the selectable flow of the detector support fluid, a carrier fluid, an analyte, and a solvent;
    a thermionic ionization detector, operably connected to the fluid mixture means and to the pneumatic controller for receiving the fluid mixture, wherein the presence of the solvent at the thermionic ionization detector occurs in a solvent elution period; and
    control means for providing said control signal so as to effect a reduction in the flow of the detector support fluid in said fluid mixture to a reduced flow for a predetermined flow reduction period, and wherein the flow reduction period is coordinated with the solvent elution period.

2. The analytical instrument of claim 1, wherein the fluid mixture means for providing the fluid mixture further comprises a separation column.

3. The analytical instrument of claim 1, wherein the flow reduction period is caused to substantially overlap the solvent elution period.

4. The analytical instrument of claim 1, wherein the fluid mixture provided to the thermionic ionization detector includes a total detector fluid flow, and the reduced flow is less than a flow rate selected from the group consisting of; a) approximately one half of the initial flow rate of the detector support fluid, and b) one percent of the total detector fluid flow.

5. The analytical instrument of claim 1, wherein the control means further comprises a computer that includes a programmable run table, and wherein the flow reduction period is provided according to the run table.

6. The analytical instrument of claim 1, wherein the detector support fluid comprises hydrogen.

7. The analytical instrument of claim 1, wherein the thermionic ionization detector further comprises:
    an ionization source having a matrix including an alkali metal compound that is capable of ionization of the analyte to produce an ion current;
    a collector electrode for receiving the ion current; and
    a fluid-directing structure for aligning the ionization source and the collector electrode in a spaced relationship and for directing the fluid mixture so as to contact the ionization source and the collector electrode.

8. An analytical method, comprising the steps of:
    providing a selectable flow of a detector support fluid;
    providing a fluid mixture including the selectable flow of the detector support fluid, an analyte, and a solvent,
    providing a thermionic ionization detector for receiving the fluid mixture wherein the presence of the solvent at the thermionic ionization detector occurs in a solvent elution period;
    effecting a reduction in the selectable flow of the detector support fluid to a reduced flow for a flow reduction period, and
    coordinating the flow reduction period with the solvent elution period.

* * * * *

UNITED STATES PATENT AND TRADEMARK OFFICE
CERTIFICATE OF CORRECTION

PATENT NO. : 5,554,540
DATED : 09/10/96
INVENTOR(S) : Chinkai Meng

It is certified that error appears in the above-indentified patent and that said Letters Patent is hereby corrected as shown below:

Column 1, line 33, "stream-" should read -- stream. --; same line, "solution" should read -- elution --
Column 1, line 44, "solution" should read -- elution --
Column 1, line 66, "solution" should read -- elution --
Column 4, line 54, "413" should read -- 4B --
Column 6, line 18, "Ns" should read -- Na --; line 34, "8" should read -- 3 --; line 49, "8" should read -- 3 --
Column 7, line 44, " F dot" should read -- F det --

Signed and Sealed this

Twenty-ninth Day of February, 2000

Attest:

Q. TODD DICKINSON

Attesting Officer

Commissioner of Patents and Trademarks